US008808301B1

(12) United States Patent
Nofsinger (10) Patent No.: US 8,808,301 B1
(45) Date of Patent: Aug. 19, 2014

(54) RAPID CUSTOM INTRA-ARTICULAR LIGAMENT RECONSTRUCTION GUIDE

(75) Inventor: Charles Nofsinger, Land O' Lakes, FL (US)

(73) Assignee: University of South Florida, Tampa, FL (US)

( * ) Notice: Subject to any disclaimer, the term of this patent is extended or adjusted under 35 U.S.C. 154(b) by 1175 days.

(21) Appl. No.: 12/537,779

(22) Filed: Aug. 7, 2009

Related U.S. Application Data

(60) Provisional application No. 61/086,949, filed on Aug. 7, 2008.

(51) Int. Cl.
*A61B 17/17* (2006.01)

(52) U.S. Cl.
USPC .......................... 606/96; 623/13.12; 382/131

(58) Field of Classification Search
USPC ..................... 606/86 R–89, 96–98, 102, 104; 623/13.11–13.2
See application file for complete search history.

(56) References Cited

U.S. PATENT DOCUMENTS

| 3,545,008 | A | 12/1970 | Bader |
| 3,882,551 | A | 5/1975 | Helmer et al. |
| 3,896,500 | A | 7/1975 | Rambert et al. |
| 3,953,896 | A | 5/1976 | Treace |
| 3,973,277 | A | 8/1976 | Semple et al. |
| 4,246,660 | A | 1/1981 | Wevers |
| 4,744,353 | A | 5/1988 | McFarland |
| 5,092,887 | A | 3/1992 | Gendler |
| 5,562,669 | A | 10/1996 | McGuire |
| 6,533,737 | B1 | 3/2003 | Brosseau et al. |
| 6,712,856 | B1 * | 3/2004 | Carignan et al. ........... 623/20.35 |
| 7,616,794 | B2 * | 11/2009 | Moeller ........................ 382/128 |
| 8,110,000 | B2 * | 2/2012 | Collins ....................... 623/13.11 |
| 8,398,645 | B2 * | 3/2013 | Aker et al. ...................... 606/88 |
| 2005/0101966 | A1 | 5/2005 | Lavallee |
| 2007/0185498 | A2 | 8/2007 | Lavallee |

OTHER PUBLICATIONS

Reider, et al., The Bankart Procedure Modified by the Use of Prolene Pull-Out Sutures, The Journal of Bone and Joint Surgery, 1982, vol. 64-A, No. 4, pp. 628-629.
Miller, et al., Cruciate Ligament Graft Intra-Articular Distances, Arthroscopy: The Journal of Arthroscopic and Related Surgery, 1997, vol. 13, No. 3, pp. 291-295.

* cited by examiner

*Primary Examiner* — Michael T Schaper
(74) *Attorney, Agent, or Firm* — Nicholas Pfeifer; Robert J. Varkonyi; Smith & Hopen, P.A.

(57) ABSTRACT

Custom surgical guides based on the patient's unique anatomy that can be quickly and accurately applied intra-operatively without navigation are disclosed. The device is created using preoperative MRI images and uniquely conforms to the bone in the region of the desired tunnel. The images are filtered and used to generate computerized three dimensional models of the patient's anatomy. The models can be introduced through a portal and applied to the bone denuded of soft tissue.

5 Claims, 10 Drawing Sheets

RAPID CUSTOM INTRA-ARTICULAR LIGAMENT RECONSTRUCTION GUIDE

CROSS REFERENCE TO RELATED APPLICATION

This application claims priority to U.S. Provisional Patent Application No. 61/086,949, entitled "Rapid Custom Intra-Articular Ligament Reconstruction Guide", filed on Aug. 7, 2008, the contents of which are herein incorporated by reference.

FIELD OF INVENTION

This invention relates to a method of generating custom surgical guides. Specifically, the invention entails using medical images of a patient to develop custom surgical guides.

BACKGROUND OF THE INVENTION

Joint damage, such as dislocation or ligament tearing, is often a result of connective tissue damage, weakening or breaking the connection between the soft tissue and bone. Resultant weakening can lead to recurring dislocation or reduced joint integrity.

For joint surgery, such as anterior cruciate ligament reconstruction surgery, a bone tunnel is formed in each of two bones of the joint. In knee surgery, these are the femur and the tibia. Preferably, the bone tunnel is formed by drilling a core out through the bone such that the core might be used to form the bone plug in the composite graft. The bone plugs are machined to form two longitudinal substantially parallel grooves opposite one another. At least one ligament replacement, such as a semitendinosus tendon, and/or gracilis, is extended between both of two bone plugs along the parallel grooves in each plug. The ligament replacement is attached to the two bone plugs. Each bone plug is inserted into one of the bone tunnels and secured therein by an interference screw. The use of the bone-tendon-bone composite graft of the invention results in a reconstructed cruciate ligament, also, in accordance with an embodiment the present invention.

Although the lengths of the anterior and posterior cruciate ligaments have been well characterized in the literature, there are few studies of the actual length of these ligaments or the size needed for reconstruction grafts. Current placement of ligament reconstruction surgery is based on current recommendations, and the intra-articular graft length less than published values for the ligaments themselves, and that the patella tendon graft is of adequate length to be used for reconstruction of these ligaments. (Miller, L., et al., Cruciate ligament graft intra-articular distances, Arthroscopy: J of Arthro & Related Surg, 13:3, 291-295).

Intra-articular entry points for ligament reconstruction was traditionally performed using landmark recognition, requiring a constant anatomical landmark, such as the intercondylar notch, to orient placement of a guide. Many times, the placement of intra-articular ligament reconstruction tunnels was too far anterior, resulting in small surgical tunnels, uneven bone plug reconstruction, and delayed graft failure. Alternatively or in conjection with landmark recognition, tunnel placement is based on computer navigation. However, landmark recognition and computer navigation assume similar patient anatomy with respect to the patient's bones and ligaments. Multiple published studies show current reconstruction technology has an inaccurate placement and therefore non-anatomic restoration of knee kinematics. Accurate ligament attachment shows improved joint kinematics. However, studies of current technologies indicate there exists a high probability for inaccurate placement during reconstruction, and therefore non-anatomic restoration of the joint. Accordingly, there exists a need for an improved ligament reconstruction guide to allow better anatomical placement during reconstruction surgery.

SUMMARY OF THE INVENTION

Accurate placement has been shown to better reproduce kinematics. This device creates a custom guide based on the patients unique anatomy that can be quickly and accurately applied intra-operatively without navigation. The device is created from preoperative MRI and uniquely conforms to the bone in the region of the desired tunnel. The device can be introduced through a portal and applied to the bone denuded of soft tissue. Computer-assisted surgical systems have been used to assist doctors during a surgical procedure, from displaying status and data on the patient's physical condition to allowing displaying computer generated models of the anatomical structures of interest to help the surgeon visualize the surgical procedure being performed, as described in U.S. Pat. No. 6,533,737 to Brosseau et al. The surgical guide consists of a body, a tooling guide, and at least one face adapted to fit the interstitial space between the bones of the joint and inversely contoured to the shape of the patient's joint anatomy, wherein the at least one face is disposed on a proximal end of the body. The tooling guide can be any tool guide known in the art, such as guide cut out, drill guide, groove tracks. Examples of tools that may be used with the guide include awl, drill, osteotome, dental hatchet, burr, and coring reamer. The guide is useful in any joint surgery and has a face that is inversely correlated with the contours of the at least one anatomical bone structure, such as the epiphysis of the tibia and the epiphysis of the fibula. Of particular note, the guide is useful for ligament reconstruction, such as anterior cruciate ligament (ACL), medial cruciate ligament (MCL) reconstruction with natural, cavadaric, or artificial ligament.

Also disclosed is a method of manufacturing the surgical guide. At least one image of the joint requiring surgery is collected using an image slice thickness of 0.499998 mm and patient image orientation of RAX. These images are used to generate a model of the joint. The location of the tooling guide is then determined based on the surgery. For example, in ligament surgery, the location is selected such that a coring hole will allow for an anatomically equivalent reconstruction. The surgical guide is then prepared, constructing the guide with a body and at least one face adapted to fit the interstitial space between the bones of the joint and inversely contoured to the shape of the patient's joint anatomy, wherein the at least one face is disposed on a proximal end of the body. The at least one tooling guide is also prepared, such that the tooling guide disposed on the distal end of the body, in the predetermined location. Exemplary tooling guides include a guide cut out, drill guide, and groove tracks.

Imaging useful in the creating of the surgical guide include magnetic resonance imaging (MRI), nuclear magnetic resonance imaging (NMRI), computed axial tomography (CAT or CT scan) scan, ultrasound, fluoroscopy, x-ray, tomodensimetric (TDM), positron emission tomography (PET), and combinations thereof. In specific embodiments, image is an MRI image acquired using a magnetic field strength of 3 tesla. The image is optionally collected at an image resolution of 512 pixels by 512 pixels and the pixel size being 0.4688 mm.

In specific embodiments of the invention, the at least one image is processed. For example at least one mask may be generated on the at least one medical image. In some embodiments, the mask is generated on top of the pixels within the contrast range of 0 to 800, 1250 to 4000, or both. Further, the at least one mask is processed to remove image artifacts. Optionally, the contours of the two bones from the image data are extracted from the image data and a reverse template of the bone contours is created. In specific embodiments of this, the image data is extracted using a Boolean extraction to create the reverse of the bone. The model of the ligament-joint may be transferred to a three dimensional printer to generate a prototype.

BRIEF DESCRIPTION OF THE DRAWINGS

For a fuller understanding of the invention, reference should be made to the following detailed description, taken in connection with the accompanying drawings, in which:

FIGS. 2(a) and (b) depict masks of the medical image pixels. (A) The image highlights the pixels of the compact bone and (B) the image highlights the pixels of spongy bone.

FIGS. 3(a) and (b) depict the masks after data processing to remove artifacts. (A) the two masks from FIG. 2 are overlaid on each other after cropping, and then (B) the two masks are merged and filled.

FIGS. 4(a) and (b) depict a computer generated mask of the bone. (A) a computer generated mask is created and used to (B) generate a reverse image of the space of the knee.

FIGS. 5(a) and (b) depict the contours of the face of the bone. (A) generating the face contour of the femoral ACL attachment point; and (B) a block of reverse contour of femoral face was generated for use in generating the face contour.

FIGS. 6(a) and (b) depict the ligament attachment point. (A) the face contour of the tibial ACL attachment point is imaged; and (B) a block of reverse contour of femoral face permits imaging the ACL's tibial attachment point.

DETAILED DESCRIPTION OF THE PREFERRED EMBODIMENT

The surgical guide is designed to register using the epiphysis or articulation of the joint, where the bones contact. The surgical guide is designed to replicate the ligament surgery plan, allowing easy identification and location of surgical site, such as bone coring. The guide is useful in any joint surgery. However, for the purposes of illustration, the guide is described while utilized in replacement of the Anterior Cruciate Ligament (ACL) of the knee by an artificial ligament and glenohumeral ligament reconstruction. Of particular note, the guide is useful for ligament reconstruction, such as anterior cruciate ligament (ACL), medial cruciate ligament (MCL), and glenohumeral reconstruction with natural, cavadaric, or artificial ligament.

As used herein, "artifact" refers to an artificial or distorted image present on a diagnostic image which is caused by an instrument, including the imaging device, procedure, or other form of intervention occurring during the imaging procedure. Artifacts include data that is not compact bone, such as other tissue with similar reaction to the imaging technique employed.

As used herein, "image" means the data that represents the spatial layout of anatomical or functional features of a patient, which may or may not be actually represented in visible, graphical form, including image data residing in a computer memory, as well as an image appearing on a computer screen. Non-limiting examples of images include an MRI image, a PET image, CAT image, ultrasound image, and the like. When using time sequence methods, such as ultrasound, as a data acquisition method, an "image" refers to one particular "frame" in the series that is appropriate for processing at that time.

As used herein, "imaging", "radiometric imaging", or "imaging modality" refers to at least one method or mechanism by which a diagnostic image of a joint is obtained. Imaging comprises use of at least one imaging method which, when performed to a subject, permits a diagnostic image of a part of the subject, including without limiting the invention, the use of static magnetic fields produced via radiofrequency pulse, x-ray radiation, or administration of a chemical entity that alters an anatomical structure allow for diagnostic image. Non-limiting examples include magnetic resonance imaging (MRI), nuclear magnetic resonance imaging (NMRI), computed axial tomography (CAT or CT scan) scan, ultrasound, fluoroscopy, x-ray, tomodensimetric (TDM), positron emission tomography (PET), and combinations thereof.

As used herein, "ligament" means a band of fibrous connective tissue composed of collagen fibers. The ligaments are connective tissue connecting bones to other bones to form a joint. Capsular ligaments surround synovial joints and act as mechanical reinforcements whereas extra-capsular ligaments join bones together and provide joint stability. "Natural ligament" means a ligament collected from a living organisms, such as autologous and allergenic sources. Other ligament sources include cadavaric and artificial ligaments. Cadavaric ligaments are ligaments collected from cadavers. Artificial ligaments are non-ligament material, and include without limiting the invention, elastomeric cords, elastomeric silicone materials and fabrics, ultra-high molecular weight polymers, like polyethylene, and demineralized bone. Nonlimiting examples of artificial ligaments may be found in Treace, U.S. Pat. No. 3,953,896; Rambert, et al., U.S. Pat. No. 3,896,500; Helmer, et al. U.S. Pat. No. 3,882,551; Semple, et al. U.S. Pat. No. 3,973,277; Bader, U.S. Pat. No. 3,545,008; Wevers, et al., U.S. Pat. No. 4,246,660; and Gendler, U.S. Pat. No. 5,092,887.

A radiometric image was collected for the patient's joint using MRI and Signa HDx 3.0T™ (General Electric Healthcare, Little Chalfont, Buckinghamshire, UK) with an image slice thickness of 0.499998 mm and patient image orientation of RAX. It is noted that these are mandatory orientations. An MRI image stack was acquired by using 3D LAVA (General Electric Healthcare, Little Chalfont, Buckinghamshire, UK) settings and a magnetic field strength of 3 tesla. The images were collected at an image resolution of 512 pixels by 512 pixels and the pixel size being 0.4688 mm.

The collected MRI image stack was then imported into Mimics version 12.01 (Materialise NV, Leuven, Belgium)

imaging software, which allows the user to generate dimensional models from medical data, view images with the full contrast levels of the MRI image stack, and allow the user visual access to all data present in the image stack. Masks were generated on top of each individual medical image, with two different masks formed on each image stack.

Figure 1:
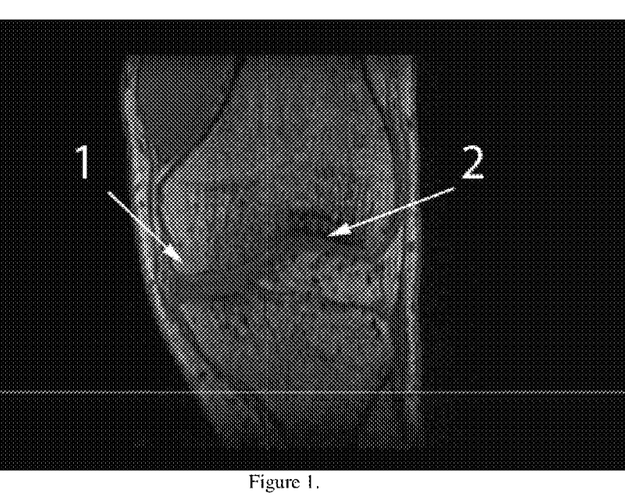
FIG. 1 depicts an image stack of 3D LAVA MRI images.
Figure 2:
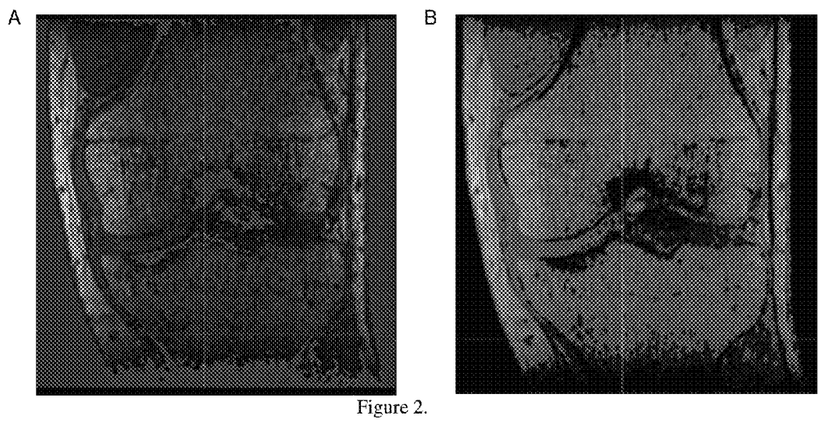

The first mask takes all of the pixels that are within the range of 0 to 800, as seen in FIG. 2(a). These pixels contain a representation of the compact bone in the image stack. However, artifacts are also collected and extracted from the mask. Similarly, the second mask is created from pixels in the top of the contrast range 1250 to 4000, seen in FIG. 2(b). These pixels contain data of the spongy bone and define the edges of bone. This mask also contains artifacts and the mask was cleaned, leaving only the bone. The use of two different masks is preferable due to the manner of MRI image stack display, some edges are well defined by a dark edge 2 while others by a light edge 1.

Figure 3:
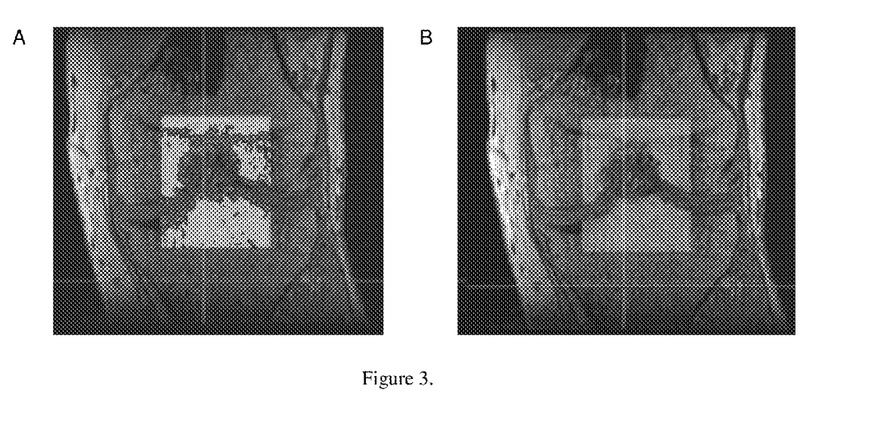
Figure 4:
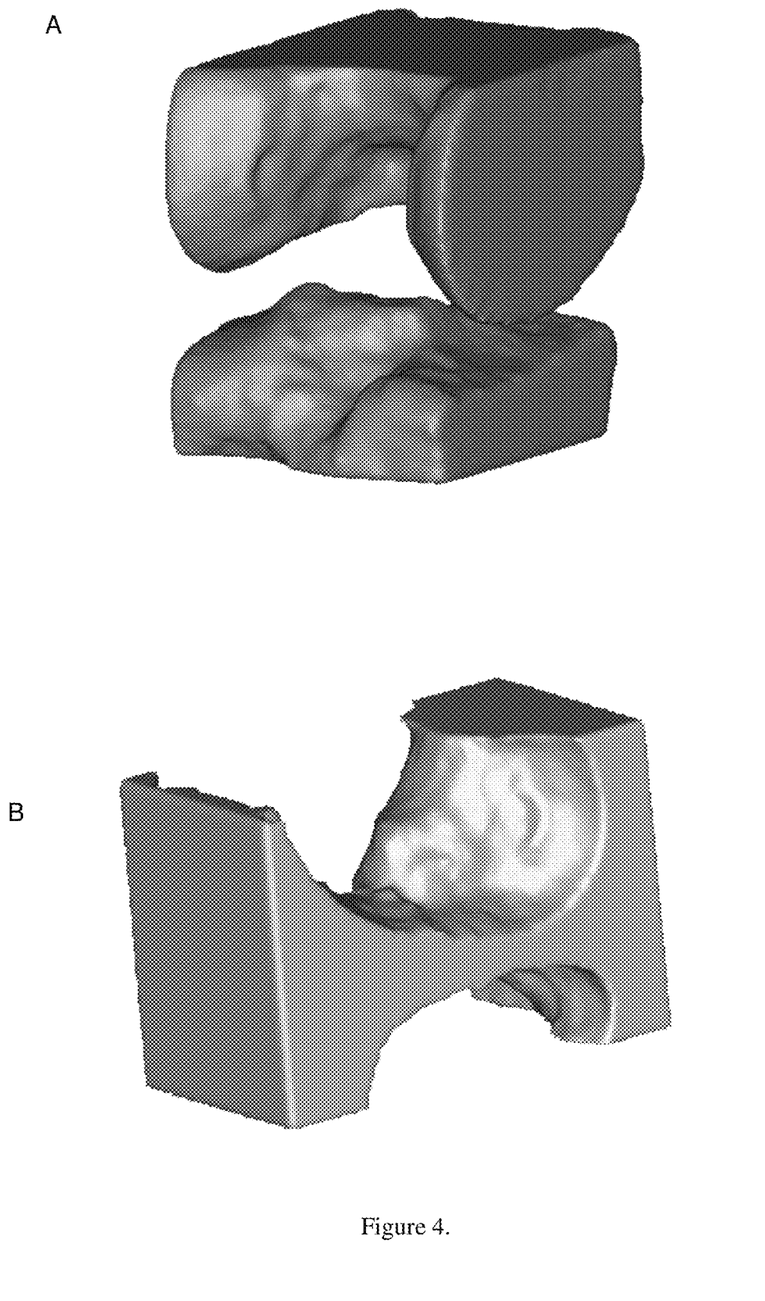

The two masks are cropped to highlight only the area of interest (the attachment points of the ACL), as seen in FIG. 3(a). The holes between the two masks are filled in and the edges are visually verified, generating a new mask seen in FIG. 3(b). An image of the highlighted area is computer generated, representing the femur and the tibia, seen in FIG. 4(a). The image is selected and a Boolean extraction is performed on the image, creating the reverse of the bone and allowing the contour of the bone to be obtained, seen in FIG. 4(b).

Figure 5:
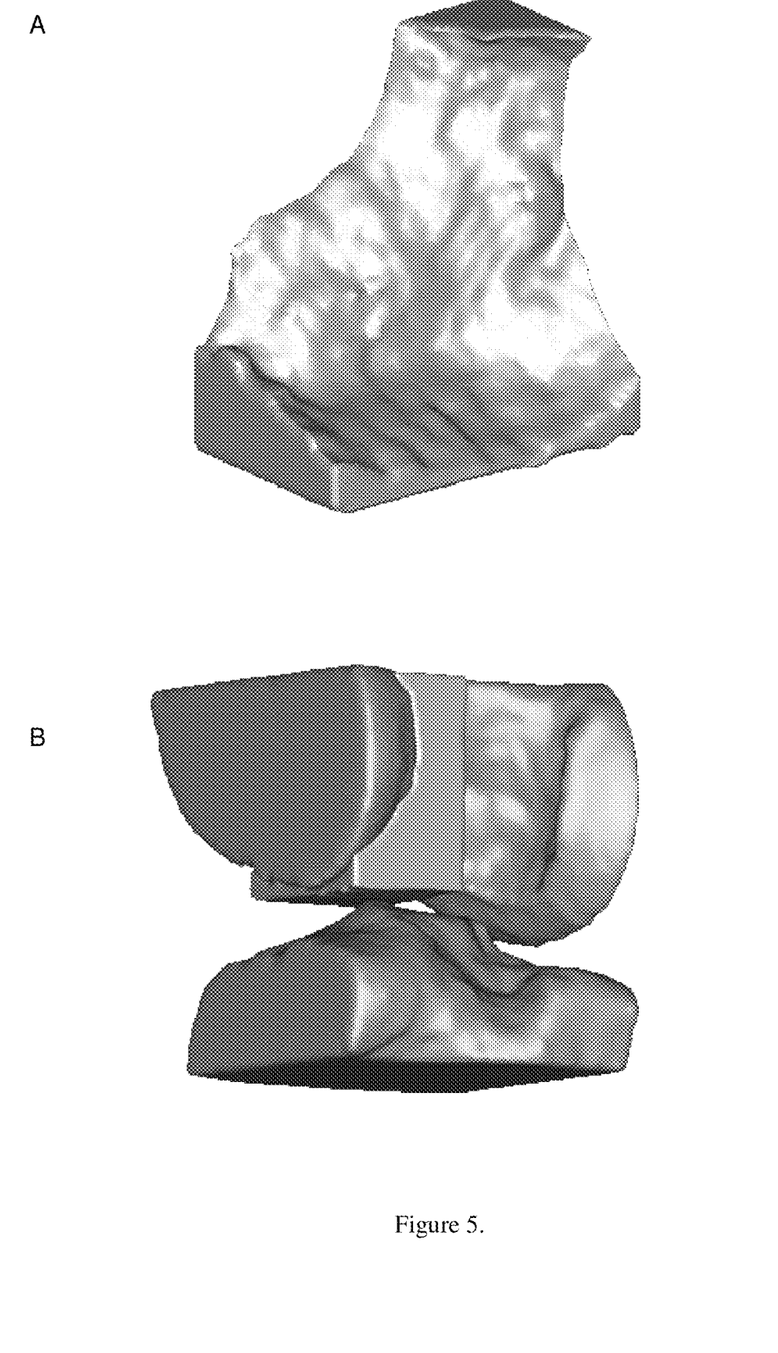

This allows visualization of the medial surface of the lateral condyle of the distal end of the femur and the proximal attachment point of the ACL on the face of the bone, seen in FIG. 5(b). The images of the object were then sliced, allowing access to the face's contour, seen in FIG. 5(a). A reverse template was then created of the area of where the ACL's true anatomical location is supposed to naturally lie.

Figure 6:
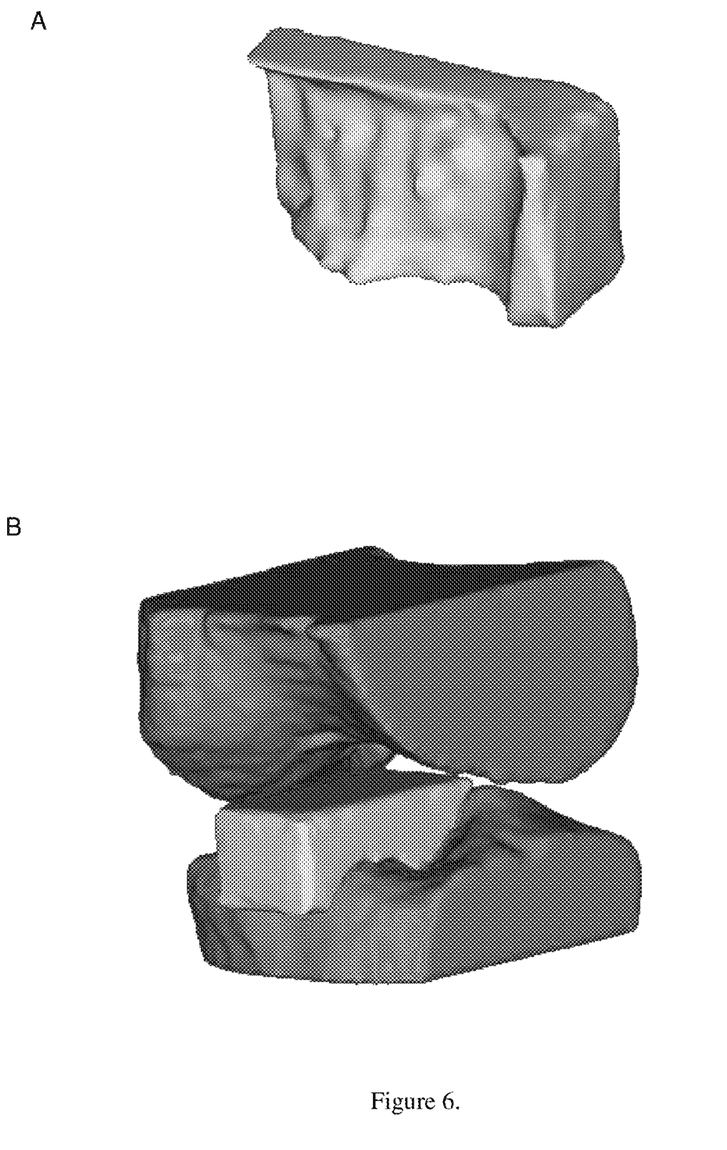

Similarly, this process was utilized to obtain information on the distal attachment point of the ACL. The front of the medial and lateral intercondylar tubercal on the tibia and behind anterior intercondyler area were analyzed, as before, to generate the ACL's distal attachment point and bone face, seen in FIGS. 6(a) and (b).

Figure 7:
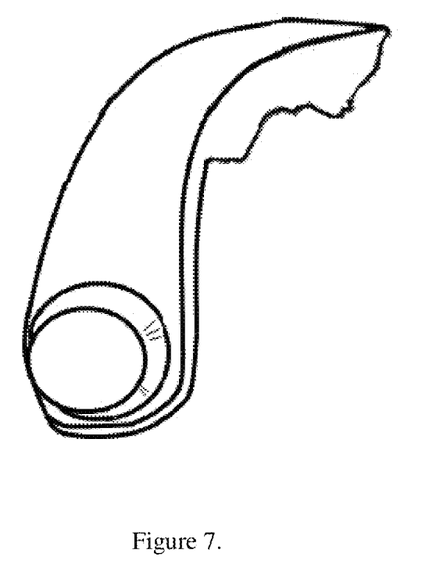
FIG. 7 depicts an illustration of a custom ligament guide.

The three dimensional models of the ACL attachment sites were then sent to a three dimensional printer that produce a prototype to the face of the model. The printer maintains accuracy to ~0.01 mm, thus maintaining the level of resolution of the created model. The ACL face models are versatile, for example tooled to insert specific guides for known surgical ACL attachment devices. For example, an ACL attachment guide was developed that fits in the interstitial space between the tibia and femur and has guide cut outs to permit proper rescission of tibial and femoral bone cores, as seen in FIG. 7. It is known in knee surgery that the ligament that joints the femur to the tibia should be placed in such a way that it respects an isometry constraint. The surgical guide allows the surgeon to ensure the isometry constraint is respected, within a pre-specified tolerance, by locating precise surgical sites. Other uses for the models may be envisioned by one of skill in the art. A placement guide is optionally added to the surgical guide.

Example 1

ACL Ligament Reconstruction

The skin surrounding the knee is retracted, and conventional surgical procedures used to excise a semitendinosus tendon, and, if desired, the accompanying gracilis. Alternatively, other ligament replacement materials may be substituted for use in the composite graft of the invention. The soft tissue surrounding the joint is resected or retracted to expose to the bony anatomy of the femur and tibia. The bony joint anatomy may be prepared by removing as much soft tissue around the femur and tibia as needed to allow for good exposure and optimal positioning and registration of the surgical guide.

Figure 8:
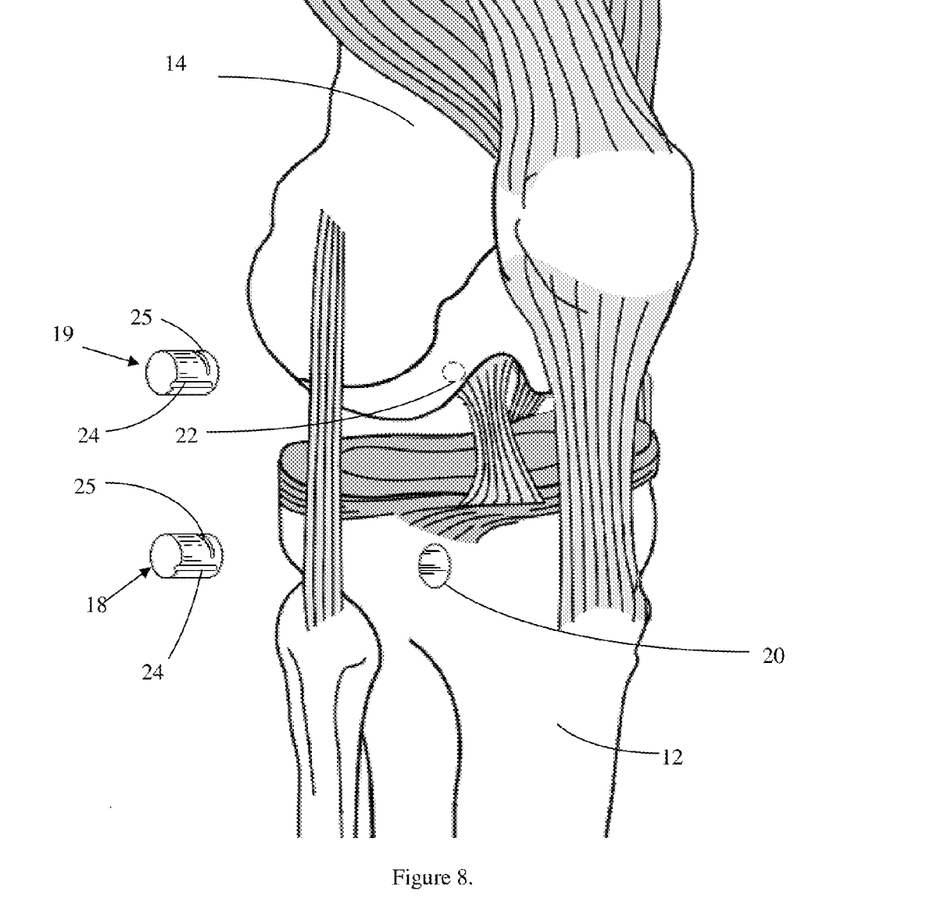
FIG. 8 depicts an illustration of the knee joint during ligament reconstruction. Bone plug are shown removed from the tibia and fibula.

The two major bones that meet at the knee joint 10 are tibia 12 and the femur 14, seen in FIG. 8. Tibial bone tunnel 20 is drilled through tibia 12 and femoral bone tunnel 22 through femur 14. Tibial bone tunnel 20 and femoral bone tunnel 22 may be formed using an awl, drill, osteotome, dental hatchet, burr, or other device known in the art, such as a coring reamer. The reamer drills out a core of bone through each of the bone tunnels, forming tibial bone core 18 and femoral bone core 19, which can be used as a bone plug in the composite graft that will be replaced when reconstructing the ligament. The surgical guide is particularly useful in coring, as it locates the drill location without need of a guide pin, which would form a stress riser in the bone plug making the bone plug subject to fracture. Further, the surgical guide properly places the drill location to ensure isometry of the reconstruction.

Figure 9:
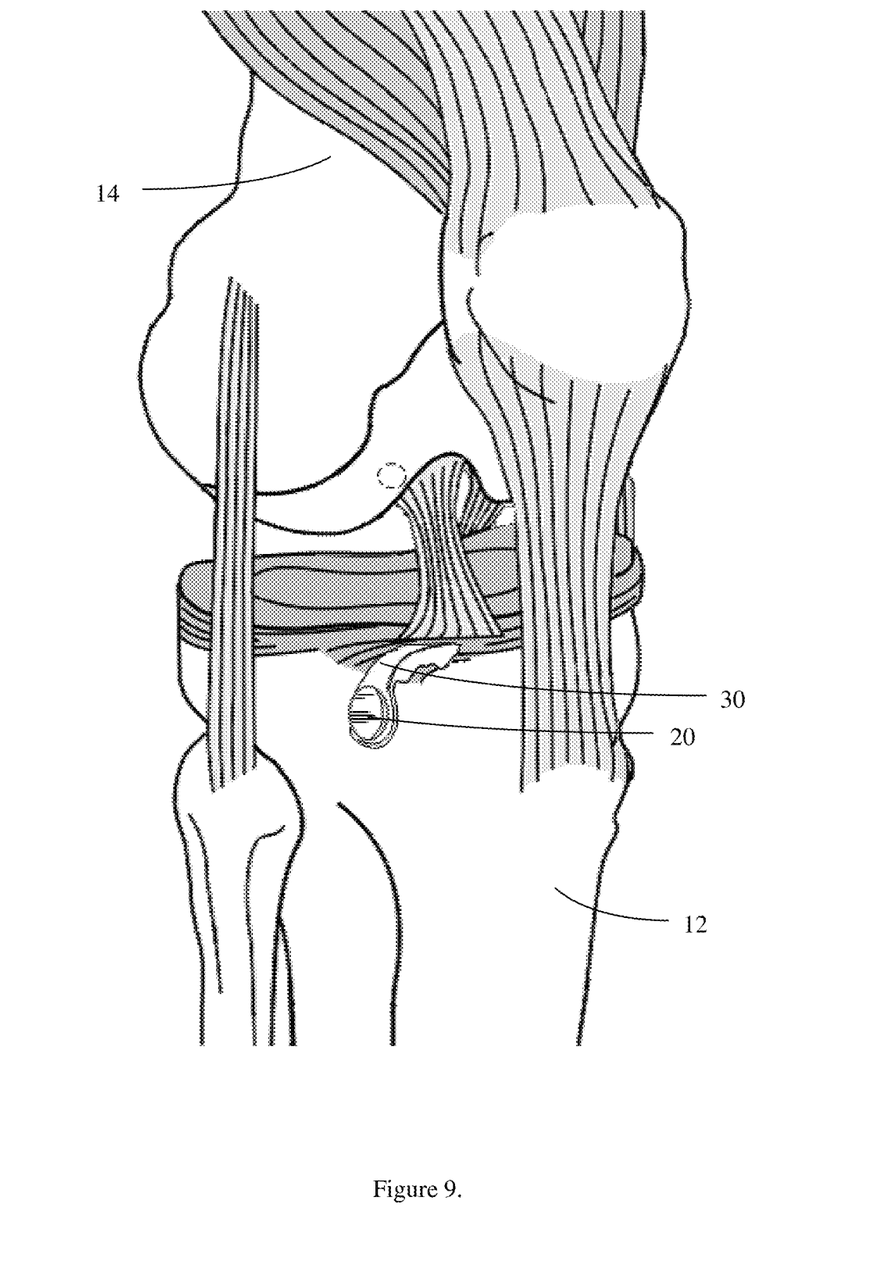
FIG. 9 depicts an illustration of the knee joint during ligament reconstruction, using the custom ligament guide to orient the surgical entry into the bone. The tibia-based guide is shown.

Surgical guide 30 is fitted into the joint, as seen in FIG. 9. The inverse joint contour 31 of surgical guide 30 is custom fit to the contours of the bone articulation, such as the epiphysis of the tibia and fibula, seen in FIG. 7. Guide cut out 32 or drill opening 33 in surgical guide 30 is disposed on pre-determined drilling locations and serves to guide a coring reamer 40 or other drill inserted therethrough. With the patient's leg held fixed, the guide can be used for drilling both the tibial tunnel and then the femoral tunnel. Therefore, a portal for the drill is not required behind the femur and a closed tunnel can be drilled. Both tunnels are drilled through the tibia from the anteromedial tibial incision. The bone cores from the reamer are removed and deburring and debridement procedures undertaken, as is known in the art.

If cores have been drilled out from the bone tunnels they may be used for the bone plugs otherwise, donor bone, namely allograft bone, can be used to make the bone plugs. Referring back to FIG. 8, regardless of the bone plug used, two longitudinal substantially parallel grooves 24 are drilled on opposite sides of each bone plug. Surgical guide 30 may have groove tracks allowing precise placement of the grooves. The grooves provide a recess in which the semitendinosus tendon 16 and gracilis 17 can be seated. Notch 25 may also be drilled, if desired, across one end of the bone plug so that the tendon can be wrapped alongside and around the end of the bone plug, without protruding excessively from the plug. Notch 25 is not required because the bone tunnel is open at each end providing no restriction on the tendon projecting above the end of the graft.

In some embodiments, suture holes 23 are provided in the bone plug, allowing attachment of the tendon to the plug. Suture holes 23 are drilled into the grooves radially through the bone plug and from one of the substantially parallel grooves 24 to the other.

Figure 10:
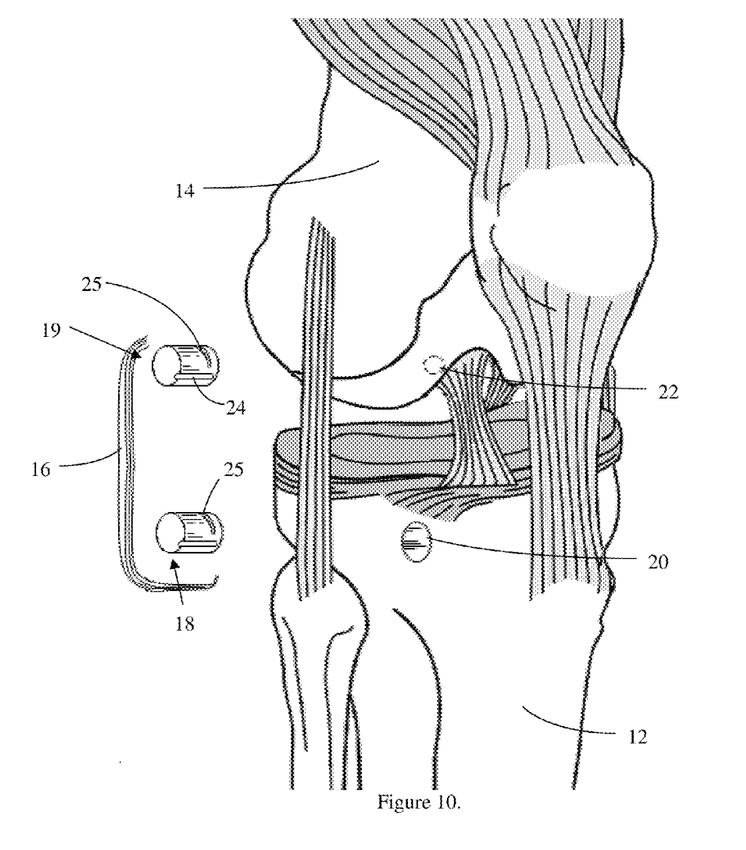
FIG. 10 depicts an illustration of the knee joint during ligament reconstruction. The replacement ligament is shown being attached to the bone plugs removed from the tibia and fibula.
Figure 11:
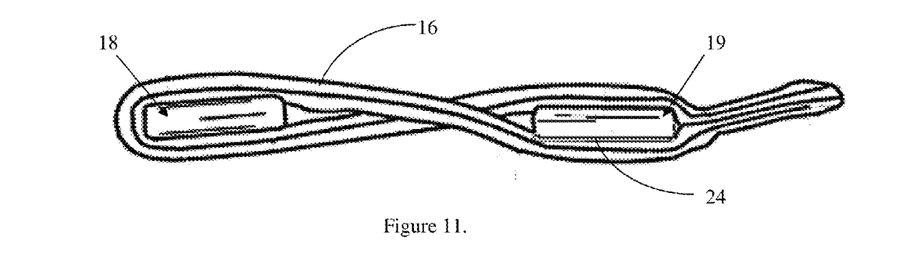
FIG. 11 depicts an illustration of the replacement ligament is shown being attached to the bone plugs.

The semitendinosus tendon 16 and/or gracilis 17 is extended between tibial bone core 18 and femoral bone core 19. The tendons are seated inside the two substantially parallel grooves 24a and b, and about an end of each bone plug, seen in FIG. 10. The tendons are sutured to themselves to form a double loop as shown in FIG. 11. Sutures are also used through the suture holes to attach the tendon to each of the bone plugs. The tendon strands may be straight or twisted between the bone plugs. Twisting will shorten the length of the graft. A ligament replacement of an embodiment of the invention may include both the semitendinosus tendon and the graeilis. As such four strands will connect the two bone plugs. Other embodiments of the invention may use one or the other of the semitendinosus tendon and gracilis. Still further embodiments of the invention may substitute or combine man-made or artificial fibers or human tissue for the tendons for use as the ligament replacement. The graft is then fixed as is known in the art, such as by fixation using a headless cannulated interference screw.

While this operation has been discussed in terms of using autogenous bone cores, alternative sources of bone plugs may be substituted. Allografts, in which donor bone is freeze-dried or fresh frozen for preservation, are one alternative. The freeze drying process kills cells in the bone and may reduce the risk of transmission of infection. Another alternative bone plug is the use of synthetic graft material. With any of these alternatives, the bone plugs may be shaped to appear as described above for the autogenous graft. With the allograft and the synthetic graft, the coring reamer is no longer required and an ordinary drill may be used instead for drilling the bone tunnels.

Example 2

Glenohumeral Ligament Reconstruction

Recurring dislocations of the glenohumeral, or "shoulder joint", typically require stabilizing the shoulder. The current "gold standard" surgery, known as the Bankart or Broca-Perthes-Bankart procedure, uses sutures and small bone anchors to reconstruct the joint. In glenohumeral embodiments of the invention, the surgical guide is custom tailored for use in reconstruction of ligaments in the glenohumeral joint, including without limiting the invention the coracohumeral ligament, coraco-clavicular ligament, caraco-acromial ligament, superior acromio-clavicular ligament, capsular ligament, glenohumeral ligaments (superior, medial, and inferior), and traverse humeral ligament. An image of the glenohumeral joint is obtained using MRI scans and Signa HDx 3.0T™ (General Electric Healthcare, Little Chalfont, Buckinghamshire, UK). Three dimensional models of the glenoid vault morphology and glenoid fossa are created using Mimics version 12.01 (Materialise NV, Leuven, Belgium) imaging software, and masks were generated on top of each individual medical image, as discussed above. The three dimensional models were then sent to a three dimensional printer that produce a prototype to the face of the model, which was then used to generate a glenohumeral attachment guide that fits in the interstitial space between the humorous and glenoid. A placement guide is optionally added to the surgical guide. Glenohumeral reconstruction can utilize any known surgical procedure known in the art, such as ACLR, Jobe, Matsen, Neer, Rockwood, and Bankart procedure. For the purposes of illustration, the invention is described in use with the Bankart procedure.

Figure 12:
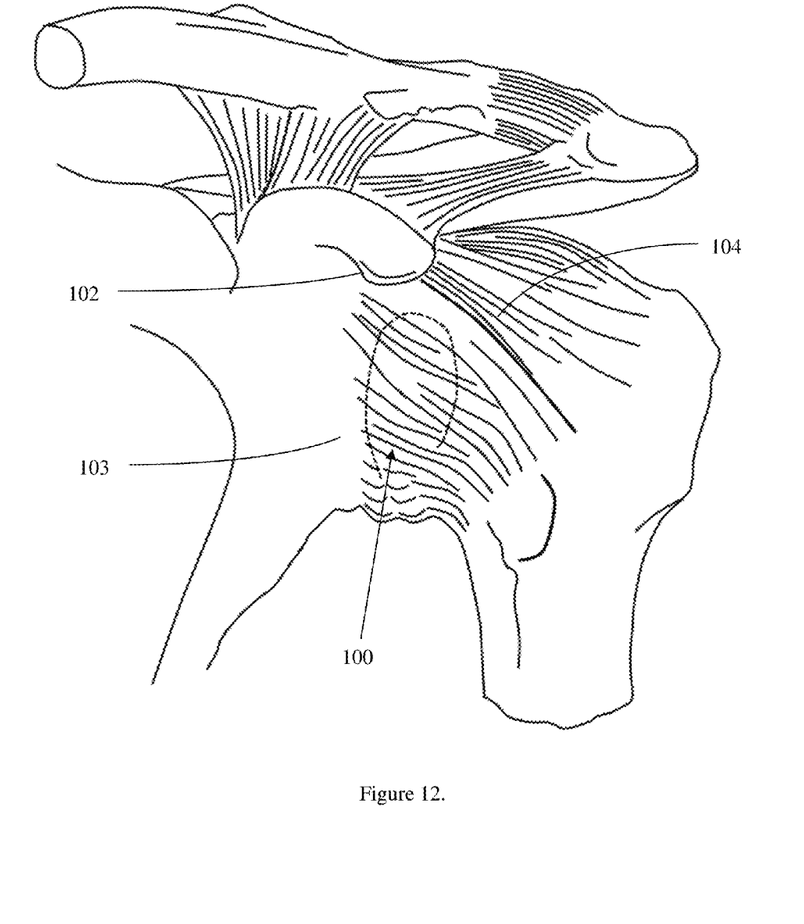
FIG. 12 depicts an illustration of the glenohumeral ligament reconstruction surgical site.

The anatomy of a dislocated shoulder of a Bankart lesion is illustrated in FIG. 12. The scapular side of the shoulder joint, the humerus and other adjacent tissue are not illustrated. Glenoid cavity 100 is normally encircled by articular capsule 101 of connective tissue attached at the margin of the cavity by the glenoid labrum 102. In the case of shoulder dislocation the labrum 102 is torn from the anterior rim 103 and inferior rim 104.

An incision is made anterior to the supraspinatus tendon through to the lateral to the middle glenohumeral ligament and the skin retracted exposing the subscapularis. The subscapularis was dissected from the scapularis and an arthroscopic elevator used to free any adhesions between the glenoid labrum 102 and the glenoid in preparation for anatomic repair of the fibrous cartilage, and to allow the glenoid labrum 102 and the glenoid capsule to "float" easily. After the overlying musculature and tendons were retracted to provide access to the shoulder joint, the glenoid capsule was then incised from the glenoid rim in accordance with the Bankart operation procedure. The scapular neck and rim are optionally roughened slightly with a burr or rasp to retain bone stock.

Surgical guide 30 is positioned between the humorous and glenoid, placing surgical markers into the proximity of the surgical site. For example, surgical guide 30 may have guide cut out 32 or drill opening 33 to permit easy and precise location of suture holes 23 into the glenohumeral bones, such as the bony surface of the glenoid rim. Once the surgical guide is placed, suture holes 23 are drilled using an awl, drill, osteotome, dental hatchet, burr, or other device known in the art, or suture anchors prepared on glenoid rim. The surgical guide is adapted to allow the drill or other device known in the art to slide within the guide cut out 32 or drill opening 33, while ensuring precise location and angulation of the suture holes. After introduction of the suture holes 23, surgical guide 30 is removed. Suture, such as an Arthrex Bio-Suture Tak (3 mm) or No. 1 Prolene mattress sutures threaded on Keith needles was pre-threaded and inserted into the suture holes located in the glenoid rim. As a result, the suture has its opposite ends extending from the suture holes, thereby providing a strong attachment for connecting the ligament to the bone structure of the glenoid rim. Additional sutures are optionally inserted through suture holes, as desired. The labrum is subsequently captured along with a "tuck" of capsule. The suture is then used to connect the lateral capsule flap to the glenoid rim. The medial flap of the joint capsule is then sutured over lateral flap, as known in the art.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a ligament guide, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of creating a surgical guide, comprising the steps of:
   imaging a patient's bone-to-bone joint;
   collecting a set of images of the patient's bone-to-bone joint;
   generating a first mask on the set of images;
   processing the first mask to remove artifacts;
   generating a second mask on the set of images;
   processing the second mask to remove artifacts;
   merging the first and second masks and cropping the merged masks to highlight attachment points of a ligament;

generating a third mask by filling in any holes between the two merged masks;

generating a three dimensional image of the highlighted ligament attachment points;

generating a reverse image of the three dimensional image of the highlighted ligament attachment points;

slicing the reverse image allowing access to contours of the bones in the reverse image;

creating a reverse template of each of the ligament attachment points;

creating a three dimensional model of each template; and generating a surgical guide from the three dimensional model of each of the templates, wherein the surgical guides each consists of a body, a tooling guide, and at least one face adapted to fit the interstitial space between the bones of the joint and inversely contoured to a shape of the patient's joint anatomy, wherein the at least one face is disposed on a proximal end of the body, and the tooling guide is disposed on a distal end of the body.

2. The method of claim 1, wherein each tooling guide is adapted to accept a tool selected from the group consisting of an awl, drill, osteotome, dental hatchet, burr, and coring reamer.

3. The method of claim 1, wherein the set of images are collected at an image resolution of 512 pixels by 512 pixels and a pixel size being 0.4688 mm.

4. A method of generating a surgical guide, comprising the steps of:

imaging a patient's bone-to-bone joint;

creating an image stack from images created in the imaging step of the patient's bone-to-bone joint;

generating a first mask on the set of images;

processing the first mask to remove artifacts;

generating a second mask on the set of images;

processing the second mask to remove artifacts;

merging the first and second mask and cropping the merged masks to highlight attachment points of a ligament;

generating a third mask by filling in any holes between the two merged masks;

generating a three dimensional image of the highlighted ligament attachment points;

generating a reverse image of the three dimensional image of the highlighted ligament attachment points;

slicing the reverse image allowing access to contours of each bone in the reverse image;

creating a reverse template of each of the ligament attachment points;

creating a three dimensional model of each template; and generating a surgical guide from the three dimensional model of each of the templates, wherein the surgical guides each consists of a body, a tooling guide, and at least one face adapted to fit the interstitial space between the bones of the joint and inversely contoured to a shape of the patient's joint anatomy, wherein the at least one face is disposed on a proximal end of the body, and the tooling guide is disposed on a distal end of the body; wherein the at least one tooling guide is adapted to accept a tool selected from the group consisting of an awl, drill, osteotome, dental hatchet, burr, and coring reamer;

the image stack is collected at an image resolution of 512 pixels by 512 pixels and a pixel size of 0.4688 mm;

the imaging is MRI and an MRI image was acquired using a magnetic field strength of 3 tesla;

the first mask is generated on top of pixels within a contrast range of 0 to 800; and the second mask is generated on top of pixels within a contrast range of 1250 to 4000.

5. The method of claim 4, further comprising extracting image data using a Boolean extraction to create the reverse template of the bone contours.

* * * * *